(12) United States Patent
Eichelberger et al.

(10) Patent No.: US 7,289,705 B2
(45) Date of Patent: Oct. 30, 2007

(54) CABLE HAVING SIGNAL CONDUCTORS SURROUNDING OPTICALLY TRANSMISSIVE CORE REMOTE IMAGING SYSTEM

(75) Inventors: Eric Eichelberger, Tualatin, OR (US); Theron V. Page, Jr., West Linn, OR (US); Chanramany Riel, Vancouver, WA (US); Kristin Ngo, Portland, OR (US)

(73) Assignee: Ludlow Company LP, Chicopee, MA (US)

( * ) Notice: Subject to any disclaimer, the term of this patent is extended or adjusted under 35 U.S.C. 154(b) by 1436 days.

(21) Appl. No.: 09/916,728

(22) Filed: Jul. 26, 2001

(65) Prior Publication Data

US 2003/0021557 A1 Jan. 30, 2003

(51) Int. Cl.
*G02B 6/44* (2006.01)

(52) U.S. Cl. .................. 385/101; 385/107; 385/116; 385/117

(58) Field of Classification Search ......... 385/100–114, 385/115–121
See application file for complete search history.

(56) References Cited

U.S. PATENT DOCUMENTS

| 3,644,659 | A | | 2/1972 | Campbell |
| 5,329,940 | A | * | 7/1994 | Adair ................. 128/200.26 |
| 5,418,878 | A | * | 5/1995 | Sass et al. ................. 385/101 |
| 5,787,217 | A | * | 7/1998 | Traut et al. ................ 385/106 |
| 5,821,466 | A | | 10/1998 | Clark et al. |
| 6,110,107 | A | | 8/2000 | Bellahsene et al. |

* cited by examiner

*Primary Examiner*—Georgia Epps
*Assistant Examiner*—M. Hasan
(74) *Attorney, Agent, or Firm*—Langlotz Patent Works, Inc.; Bennet K. Langlotz

(57) ABSTRACT

An optical imaging system with a flexible cable having a first end and a second end. The cable has a central core element including a flexible optical conduit, with a number of wires surrounding the core element to form a tube concentric with an axis defined by the center of the core. The cable has a conductive shield layer surrounding the wires and uniformly spaced apart from the wires. An electronic instrument is connected to the first end of the cable and has an illuminator coupled with the optical conduit and a display device connected to the wires. An image transducer is connected to the second end of the cable and is connected to the wires. The wires may be twisted pairs evenly spaced apart from each other, and evenly spaced apart from an axis defined by the core.

20 Claims, 4 Drawing Sheets

CABLE HAVING SIGNAL CONDUCTORS SURROUNDING OPTICALLY TRANSMISSIVE CORE REMOTE IMAGING SYSTEM

FIELD OF THE INVENTION

This invention relates to multiple-wire cables, and more particularly cables for remote imaging systems.

BACKGROUND OF THE INVENTION

Remote imaging systems are used to view objects not normally accessible to human observation or conventional imaging tools. Only limited-size image transducers are positioned for viewing, and a signal is transmitted to a remote location for viewing. For instance, surgeons use optical probes to view internal anatomy for diagnosis or surgery. Such systems require miniaturized multi-wire cable assemblies to transmit images recorded by a charge coupled device (CCD) to an external display screen.

For surgical and other applications, it is desirable to minimize the cable size. Limited diameter facilitates desired flexibility. However, a detailed real-time image needs significant bandwidth, requiring many separate conductors of a given frequency capability. To avoid undesirably bulky cables when substantial numbers of conductors are required, very fine conductors are used. To limit electrical noise and interference at high signal frequencies, conductors are generally shielded. A typical approach employs fine coaxial wires, which are bundled in a cable. Each wire includes its own shield, which provides suitable protection against interference at high frequencies.

While adequate, multiple coaxial assemblies have several disadvantages. The manufacturing cost of fine coaxial wiring is higher than is acceptable for many applications. The mode of terminating very fine coaxial wire is complex and expensive. And coaxial wires generate unwanted bulk due to the need for a given spacing between core conductor and shield.

For low-voltage differential signal (LVDS) communication, twisted pair wiring has been used effectively. However, for the finest gauge wires and for high frequencies required in certain applications, twisted pair wires have critical limitations. One problem is that when twisted pairs are bundled together and surrounded by a suitable conductive shield layer, they have different electrical characteristics with respect to the shield. Some pairs will inevitably be closer to the shield than are others, resulting in common mode impedance differences or signal skew as signals via different pairs arrive at different times. Such skew limits usable signal rates, a particular concern with very small conductors needed for slim, flexible cables requiring a multitude of lines.

A further disadvantage of existing systems is that they lack a light source, requiring a second cable in the surgeon's hand to convey light via an optical fiber bundle. Coordination of separate cables makes surgery is difficult, and requires a larger surgical opening in the patient. Moreover, efforts to unify the two cables create a much stiffer cable lacking desired flexibility due to its overall size.

SUMMARY OF THE DISCLOSURE

The present invention overcomes the limitations of the prior art by providing an optical imaging system with a flexible cable having a first end and a second end. The central has a cernral core element including a flexible optical conduit, with a number of wires surrounding the core element to form a tube concentric with an axis defined by the center of the core. The cable has a conductive shield layer surrounding the wires and uniformly spaced apart from the wires. An electronic instrument is connected to the first end of the cable and has an illuminator coupled with the optical conduit and a display device connected to the wires. An image transducer is connected to the second end of the cable and is connected to the wires. The wires may be twisted pairs evenly spaced apart from each other, and evenly spaced apart from an axis defined by the core.

DETAILED DESCRIPTION OF A PREFERRED EMBODIMENT

Figure 1:
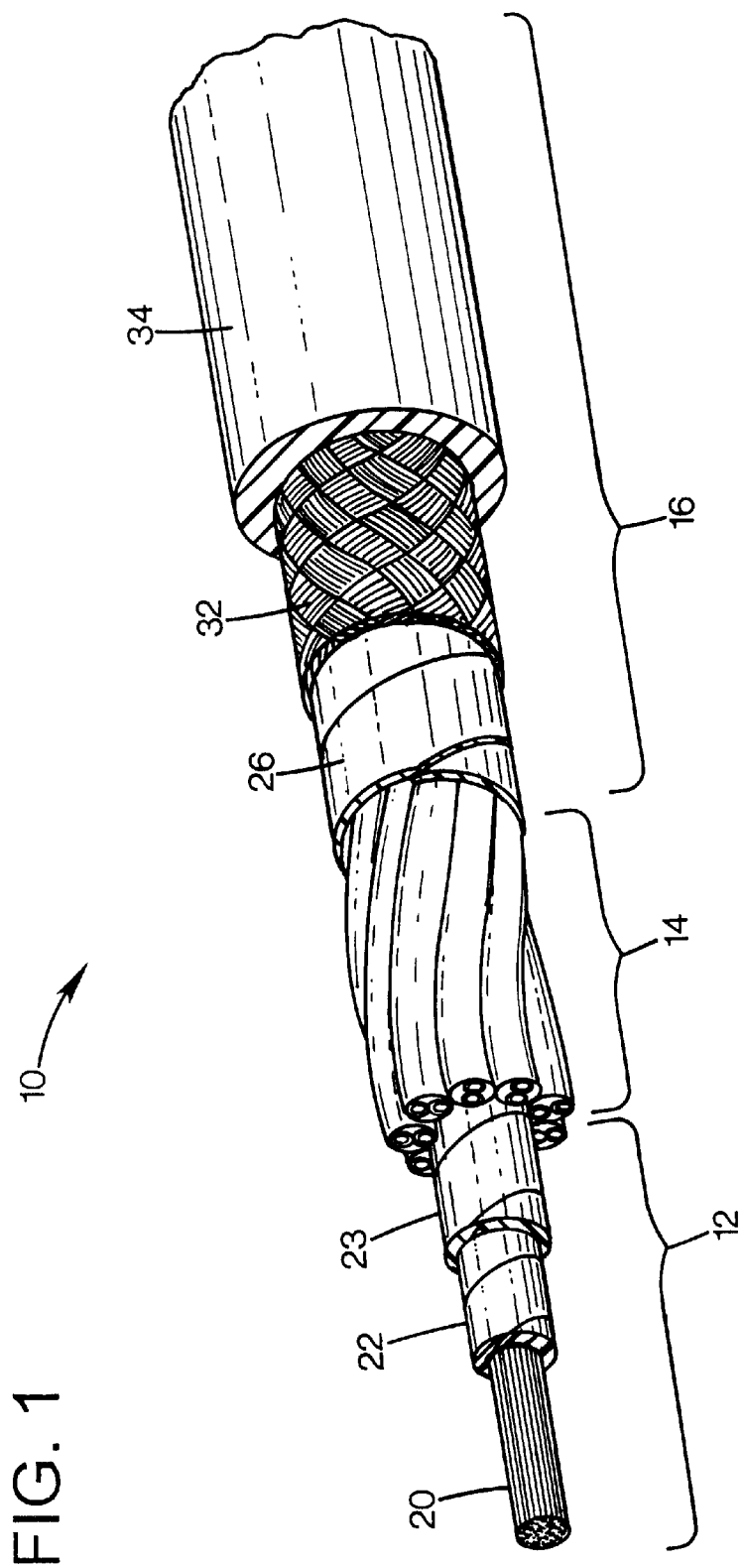
FIG. 1 is a cut-away perspective view of a cable assembly according to a preferred embodiment of the invention.

FIG. 1 shows a flexible cable assembly 10 for high frequency signal or high speed data transmission. The cable includes a core 12, a set of twisted pair wires 14 helically wrapped about the core, and an outer sheath portion 16.

The core has a flexible optical conduit provided by bundle of light-transmissive optical fibers 20. The fibers are wrapped by a spiral metal armor layer 22 with an inside diameter of 0.160, and an outside diameter of 0.200. The armor layer serves to provide a cylindrical shape that does not deviate in cross section significantly under later pressure, to preserve uniform spacing of the pairs from the axis of the cable. The armor is insulated by a helically-wrapped single band of thin tape 23. The tape is a low-friction fluoropolymer film having a thickness of 0.002 inch, a width of 0.125 inch, and wrapped with 45% overlap. In the preferred embodiment, the conduit is provided by 2050 fibers, each of 0.66 Numerical Aperture and having a 70 micron diameter, with a fiber packing density of 80%, for an overall diameter of 3.5 mm.

The twisted pair wires 14 each include two helically twisted wires insulated from each other and encased in a conformal pair sheath as will be discussed below. Nine twisted pairs are provided, although this number may vary without limitation depending on the needs of the particular application. Each twisted pair sheath has a diameter of 0.030 inch, which allows each to abut the surface of the core throughout its entire length, and to abut each adjacent pair sheath. This ensures that each pair is kept at the same controlled distance from the core conductor, and from the adjacent pairs.

In the preferred embodiment, the pairs wrap helically about the core. The wrap angle results in each pair making one full wrap about the core over a cable length of 2.0 inches. The wrap angle may vary slightly to accommodate variations in pair sheath diameter and core sheath diameter. If the pairs were sized to abut each other and the core, a slight variance of the pair diameter above nominal, or of the core diameter below nominal would cause at least one pair to be forced away from abutment with the core. However, an intended slight under-sizing of the pairs (and/or over-sizing of the core) prevents this problem. In this case, the expected gapping between pairs that would occur if they were parallel to the core is prevented by helically wrapping them. The degree of the wrap angle is in effect determined by the geometry of the pairs and core, with the wrap angle increasing (and the length for one full helical revolution of a pair decreasing) for smaller pair diameters.

The twisted pairs are helically wrapped by a single band of thin tape 26 that holds the pairs against the core during intermediate manufacturing stages, and throughout the life of the cable. The tape is slightly tensioned to bias the pairs against the core, and to prevent gapping when the cable is flexed during usage. The tape is a low-friction fluoropolymer film having a thickness of 0.004 inch. With a tape width of 0.5 inch, and an outside diameter of the pair and core bundle of 0.290 inch, the tape wraps with approximately 3 turns to the inch, with a 30% overlap between wraps.

A conductive shield 32 wraps closely about the bundle. The shield is a braided wrap of 38 AWG copper wire, with a specified coverage of at least 90%. With the controlled dimensions of the spacer sheath, the shield is spaced equally from each wire pair.

An outer sheath 34 closely surrounds the shield with a wall thickness of 0.030 inch, and provides protection against damage. The outer sheath is formed of flexible polyurethane, and is preferably co-extruded about the shield. The finished cable has an exterior diameter of 0.390 inches.

Figure 2:
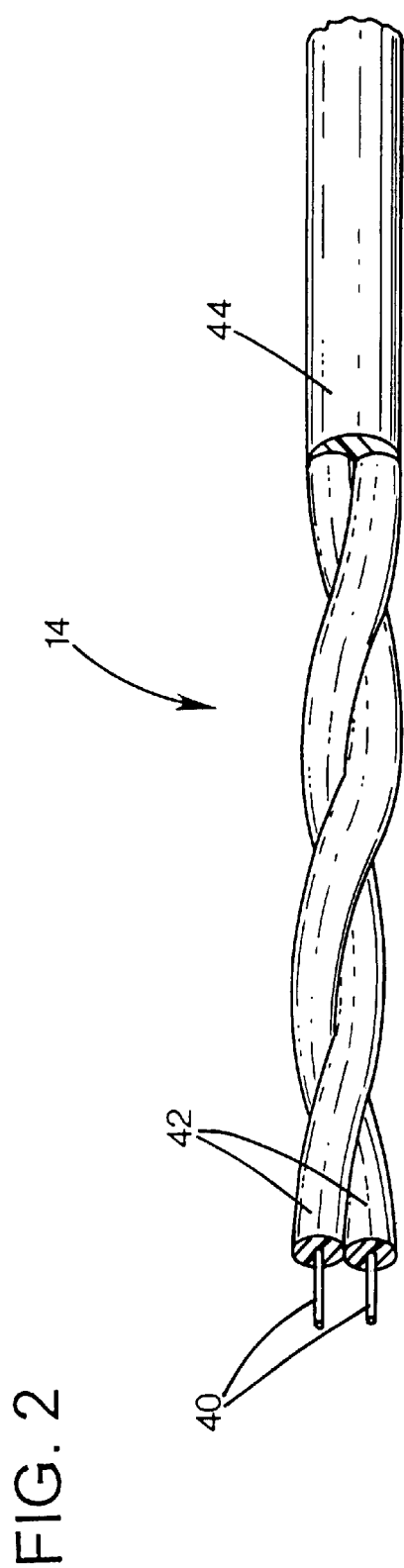
FIG. 2 is a cut-away perspective view of a cable assembly component according to the preferred embodiment of the invention.
Figure 3:
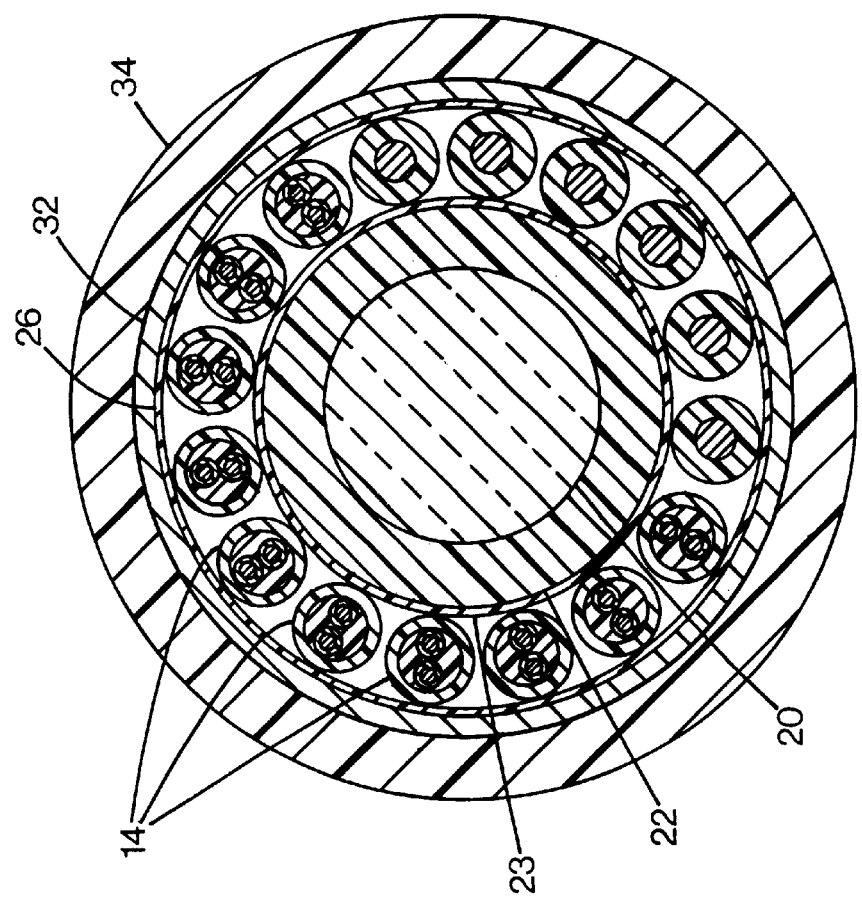
FIG. 3 is a sectional end view of a cable assembly according to the preferred embodiment of the invention.

FIG. 2 shows a single twisted pair 14 in detail. Each wire of the pair has a conductor 40 of 32 AWG copper, surrounded by an insulating sheath 42 of 0.003 inch wall thickness fluropolymer material. Each sheathed wire has an outside diameter of 0.015 inch. The wires are wound in a helix with a twist rate of 3 full turns per inch. In some applications, the twist rates may be engineered at different rates to avoid unwanted interference between adjacent pairs. In alternative embodiments, the twist rates may alternate between two different values so that adjacent pairs do not interact. The wires are in contact with each other along their entire length, on an axis. In the preferred embodiment, the wires are encased in a cover 44 of polymeric material. The cover is co-extruded about the wires, with an outside diameter of 0.045 inch, or 1½ times the diameter of the pairs.

As illustrated and described in the preferred embodiment, it has been found that the cable enables data rates of 100 to 655 Mbits/sec per pair. This is for cables with a length of 18 to 120 inches. While the very fine wires employed are needed to ensure flexibility for applications where a connected component must be moved comfortably (such as for input devices or transducers connected to computing equipment or electronic instruments), it is believed that longer cable lengths required for other purposes will require larger conductors. Although these may employ the concepts disclosed and illustrated for the preferred embodiment, they are less suited where repeated flexibility is needed.

Figure 4:
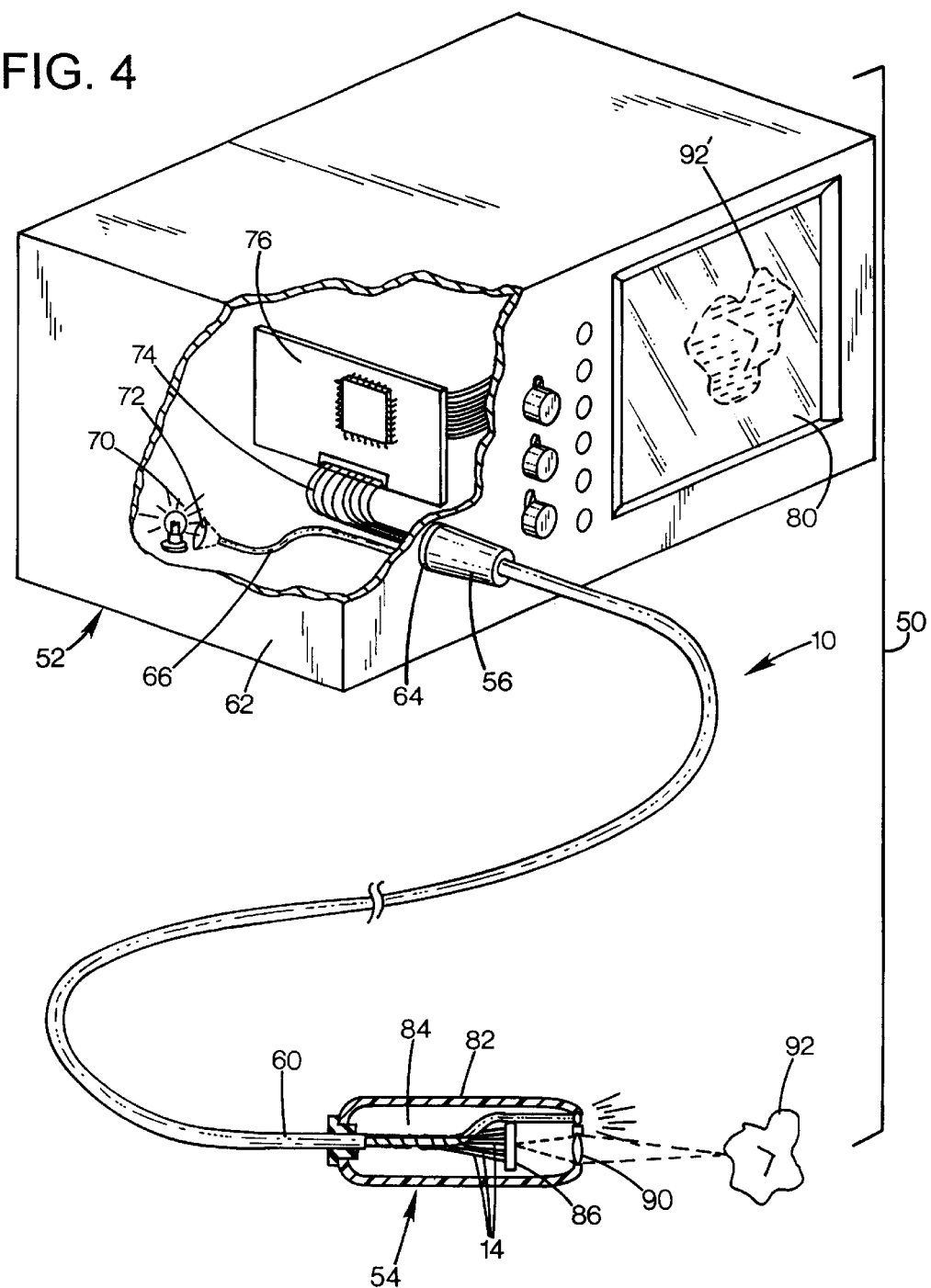
FIG. 4 is a cut-away perspective view of an imaging system employing the cable assembly according to the preferred embodiment of the invention.

The cable 10 is employed in an imaging system 50 as shown in FIG. 4. The system includes an instrument 52, the cable 10, and a camera 54. The cable 10 has a first end 56 connected to the instrument, and a second end 60 connected to the camera.

The instrument has a housing 62 with a connector 64. A fiber optic conduit 66 extends within the housing from the connector 64 to an illumination source such as a light bulb 70, via a concentrating lens 72 that couples the light source to the conduit. A set of electrical wires 74 extends from the connector to an electronic circuit element 76 in the housing. An electronic display screen 80 is electronically connected to the circuitry. The circuitry serves to receive an electronically encoded moving image information via the cable, and decodes it for display on the screen.

The instrument connector includes an interface suitable for coupling the optical conduit 66 in the housing with the optical fiber bundle 20 of the cable. Similarly, the connector includes components to connect the wiring 74 with the wires of the cable. In an alternative embodiment, the cable may be permanently attached to the housing, so that no connector is required, and so that the optical fibers extend fully to the light source, and the cable wires connect directly to the circuitry.

The camera 54 is a compact device having a housing 82 defining a chamber 84 in which a charge-coupled device (CCD) 86 is contained. In alternative embodiments, any electronic image transducer suitable for generating an electronic signal that may be decoded for re-generation of an image formed on the transducer surface may be employed. A lens 90 in the housing is positioned on axis with the imaging surface of the CCD, to form an image of an object 92 on the imaging surface. The wires 14 of the cable are connected to the CCD, so that a corresponding electronic image 92' is displayed on the screen 80.

Illumination of the object is provided by the light transmitted by the fiber optic bundle. The end of the fiber bundle 20 is located adjacent to the imaging lens 90, so that emitted light shines in the direction of the optical axis of the lens. In an alternative embodiment, the fiber ends may be distributed coaxially about the imaging lens. In operation, the camera is positioned away from the instrument, and adjacent to the object imaged. In medical applications, the camera may be internally positioned in a patient. The camera may be mounted together with surgical instruments such as endoscopes.

While the above is discussed in terms of preferred and alternative embodiments, the invention is not intended to be so limited. For instance, sensors or elements requiring the protection of the spiral armor may be substituted for the optical fiber bundle.

What is claimed is:

1. A cable assembly comprising:
   a central optically transmissive flexible core element;
   a plurality of twisted pairs of wires surrounding the core element; and
   the twisted pairs substantially evenly spaced with respect to each other to form a tube about the core.

2. The assembly of claim 1 wherein the twisted pairs abut each other.

3. The assembly of claim 1 wherein the twisted pairs abut the core.

4. The assembly of claim 1 wherein the twisted pairs are substantially evenly spaced apart from an axis defined by the core.

5. The assembly of claim 1 wherein the core includes a bundle of optical fibers.

6. The assembly of claim 1 including a conductive shield layer surrounding the twisted pairs and substantially evenly spaced apart therefrom.

7. The assembly of claim 1 including an illumination source coupled to the core at a first end of the cable, and an optical transducer connected to the twisted pairs at an opposed second end of the cable.

8. The assembly of claim 7 including a display device connected to the twisted pairs at a second end of the cable.

9. The assembly of claim 1 wherein each wire is encapsulated to form a cylindrical outer surface.

10. A cable assembly comprising:

a central core element including a light transmissive optical conduit;

a plurality of electrically conductive wires surrounding the core element;

the wires being substantially evenly spaced apart from the core to form a tube about the core; and the wires being substantially evenly spaced apart with respect to each other.

11. The assembly of claim 10 wherein the twisted pairs abut each other.

12. The assembly of claim 10 wherein the twisted pairs abut the core.

13. The assembly of claim 10 wherein the wires abut each other.

14. The assembly of claim 10 wherein the core includes a bundle of optical fibers.

15. The assembly of claim 10 including a conductive shield layer surrounding the wires and substantially evenly spaced apart therefrom.

16. The assembly of claim 10 including an illumination source coupled to the core at a first end of the cable, and an optical transducer connected to the wires at an opposed second end of the cable.

17. The assembly of claim 10 including a display connected to the wires and operable to display an image generated by the transducer.

18. The assembly of claim 10 wherein the wires are each twisted pairs of wires.

19. An optical imaging system comprising:

a flexible cable having a first end and a second end;

the cable having a central core element including a flexible optical conduit;

the cable including a plurality of wires surrounding the core element to form a tube concentric with an axis defined by the center of the core;

the cable including a conductive shield layer surrounding the wires and substantially uniformly spaced apart therefrom;

an electronic instrument connected to the first end of the cable and having an illuminator coupled with the optical conduit and a display device connected to the wires; and an image transducer connected to the second end of the cable and connected to the wires.

20. The system of claim 19 wherein the wires are twisted pairs substantially evenly spaced apart from each other, and evenly spaced apart from an axis defined by the core.

\* \* \* \* \*